United States Patent [19]

Schoenwald et al.

[11] Patent Number: 4,623,664

[45] Date of Patent: Nov. 18, 1986

[54] OIL SUSPENDED PHENYLEPHRINE

[75] Inventors: Ronald D. Schoenwald, Iowa City, Iowa; Du-Shieng Chien, Formosa, Taiwan

[73] Assignee: University of Iowa Research Foundation, Iowa City, Iowa

[21] Appl. No.: 793,138

[22] Filed: Oct. 31, 1985

[51] Int. Cl.⁴ .......................................... A61K 31/135
[52] U.S. Cl. .................................... 514/653; 514/912
[58] Field of Search ............................... 514/653, 912

[56] References Cited

U.S. PATENT DOCUMENTS

| 1,890,860 | 12/1932 | Omohundro | 514/653 |
| 3,149,035 | 9/1964 | Riegelman | 514/653 |
| 3,172,816 | 3/1965 | Swintosky | 514/653 |
| 3,515,781 | 6/1970 | Steinberg | 424/37 |
| 3,908,017 | 9/1975 | Hussain et al. | 424/311 |
| 4,001,388 | 11/1977 | Shell | 424/14 |
| 4,271,143 | 6/1981 | Schoenwald et al. | 424/78 |
| 4,469,706 | 9/1984 | Nathanson | 424/330 |

OTHER PUBLICATIONS

Handbook of Ocular Pharmacol., 2nd ed.—1978, p. 228, PSG Publishing Co., Inc.—Littleton, Mass.
Ocular Pharmacol., 4th ed.—1978, pp. 236–238, The C. V. Mosby Co.—Saint Louis.
Chem. Abst. 82: 116057(w) (1975)—Hardberger et al.

Primary Examiner—Douglas W. Robinson
Attorney, Agent, or Firm—Zarley, McKee, Thomte, Voorhees & Sease

[57] ABSTRACT

An oil suspension, preferably sesame seed oil suspension, of the base form of phenylephrine as an opthalmic medicament. Surprisingly, the base form of phenylephrine is much quicker absorbed into the eye than the conventional acid salt form. As a result, lower dosage levels can be used to achieve the same mydriatic effect, thus reducing the risk of adverse side effects from systemic absorption.

11 Claims, 3 Drawing Figures

OIL SUSPENDED PHENYLEPHRINE

BACKGROUND OF THE INVENTION

The present invention relates to a novel pharmaceutical composition containing the base form of phenylephrine. Phenylephrine has the formula 3-hydroxy-α-[(methylamino)methyl]benzyl alcohol.

Phenylephrine is a well-known pharmaceutically active amine whose principal use in the field of ophthalmology is as a mydriatic. There are, however, certain known disadvantages associated with the use of phenylephrine as a mydriatic agent. Those disadvantages, involving systemic side effects, have limited the use of this highly effective drug. Thus, in spite of the fact that it is one of the most effective mydriatics available, its use is significantly limited because of the significant side effects which may occur in some individuals treated with phenylephrine. Those unwanted significant side effects range from hypertension, syncope, and even in some cases to myocardial infarction, leading to death.

Phenylephrine HCl is a very hydrophilic drug used in the eye for its mydriatic and capillary decongestion effects. Because of its hydrophilic characteristics, it poorly penetrates the epithelium of the cornea, therefore, a relatively high concentration, 2.5% or 10%, must be applied to the eye topically to achieve a potent effect. As a result of applying a large dose which is poorly absorbed, the earlier mentioned significant systemic side effects may occur. However, because phenylephrine is such an effective mydriatic agent, despite the potential risk of adverse side effects, there is a continuing need for its use. In the past there have been some attempts to prepare prodrugs of phenylephrine in order to minimize the side effect risk. While the preparation of prodrugs is often advantageous, it is not without is disadvantages from time to time. For example, there is an increased cost factor with the preparation of prodrugs of phenylephrine. Accordingly, it can be seen that there is a continuing and real need for a technique which allows one to use phenylephrine in a topical ocular dose form which maximizes mydriatic effectiveness so that lower levels of the active drug can be employed.

Clearly, then, there is a need to reduce the systemic side effects of phenylephrine. Theoretically this could be accomplished by increasing the ocular absorption and thereby reducing systemic absorption. However, the reduction in systemic side effects is an indirect effect of improved ocular absorption. This is exemplified by the fact that even though ocular absorption may double from 2 to 4%, systemic absorption decreases from 98% to only 96%, which is not a significant decrease with respect to systemic side effects. Nevertheless, by increasing the absorption two-fold, the dose can be reduced by one-half to achieve the same therapeutic effect and in this manner systemic effects can be reduced substantially.

This invention has as its primary objective the development of new and useful phenylephrine topical compositions which when used at mydriatically effective levels allow a lower dosage level to be instilled in the eye, leading to decreased side effect risk.

Another objective of the present invention is to provide a safe and pharmaceutically effective mydriatic which is a combination of phenylephrine in the base form and a vegetable oil carrier.

Yet another objective of the present invention is to prepare a mydriatic composition for topical ocular treatment, useful in ophthalmic diagnosis and surgery, which uses phenylephrine in the base form, allowing it to be more effectively absorbed than in the acid form.

Another objective of the present invention is to provide an ocular composition which will allow phenylephrine to be used in its base form to produce a local or systemic physiological effect, similar to that achieved by much higher concentrations of acid or salt forms of phenylephrine.

An even further objective is to develop a drug delivery system for phenylephrine, adopted to improve the drug absorption, and yet maintain drug potency.

The method and manner of accomplishing these and other objectives of the present invention will become apparent from the detailed description which will follow hereinafter.

SUMMARY OF THE INVENTION

This invention relates to topical phenylephrine composition useful as a mydriatic. Phenylephrine, in its base form, is suspended in an oil suspension, either a mineral oil or vegetable oil. As a result, when used topically, the oil suspension overwhelms the buffer capacity of the tears, so that the base form actually raises the pH of the tears thereby promoting the formation of the un-ionized base form phenylephrine which is preferentially absorbed into the eye quicker than the ionized acid or salt form. Since the base form is more quickly absorbed across the cornea than the acid form, lower dosage levels can be used, reducing the risk of adverse systemic effects.

DETAILED DESCRIPTION OF THE INVENTION

Figure 1:
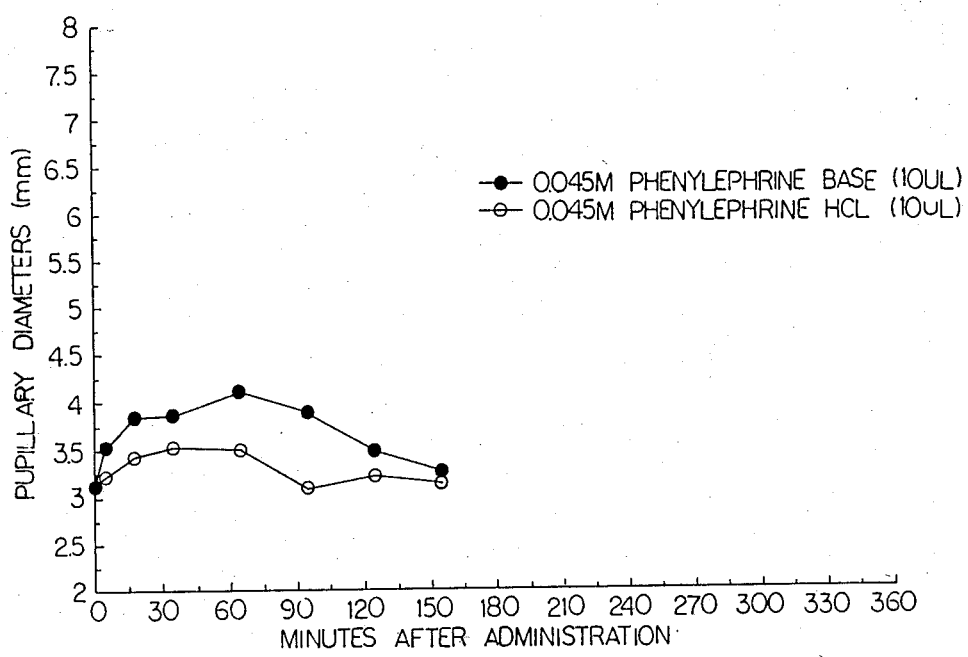
FIG. 1 shows a pupil dilation study for phenylephrine base form in comparison with phenylephrine acid form at the same molar concentration, 0.045 molar, and in the same sesame oil vehicle.

One successfully obtains the objects of the present invention by preparing a topical ocular medicament containing phenylephrine in an oil suspension system. Importantly, the phenylephrine must be in the base form, as opposed to the acid or acid salt form. In other words, the phenylephrine must be in the un-ionized form. In the past phenylephrine has always been used in its salt form since the latter is soluble and stable in buffered aqueous vehicles. In fact, the use of the base form in buffered aqueous vehicles produces the same amount of ionized species as produced from the salt form. Regardless of the initial pH of the phenylephrine salt (or base) form in the aqueous solution, the buffer capacity of the tears would overwhelm the pH of the instilled aqueous drop and poor absorption would result. In the past it has been common to use nontoxic salt forms of phenylephrine prepared by reacting it with inorganic acids such as hydrochloric acid, hydrobromic acid, sulfuric acid, sulfamic acid, phosphoric acid, nitric acid, and the like. Such acid/salt forms can be used in aqueous systems or often in the form of a viscous gel for placement in the conjunctival sac. However, the amount of phenylephrine used in such acid systems must necessarily be high, i.e. up to 10%. Conventionally, it had been thought necessary to achieve an effective mydriosis to use the high concentration of the acid form to overcome both the known poor penetration characteristics of the epithelium of the cornea and the natural buffering effect of tears.

It has now been surprisingly found that the base form of phenylephrine can be used to provide mydriatically effective topical dose compositions. In accordance with this invention, while applicant does not wish to be bound by any theory, it is believed that the base form of phenylephrine suspended in an oil suspension simply overwhelms the buffer capacity of the tears. As a result there is a high available amount of un-ionized phenylephrine which is preferentially absorbed. This only occurs in an oil suspension, not in aqueous systems, where because of the buffer capacity of tears, the pH remains unchanged.

Generally it has been found that the topical compositions of this invention may be satisfactorily prepared using either a mineral oil or an edible vegetable oil. Preferred oil suspensions include the usual triglyceride vegetable oils, preferably the edible oils such as sesame seed oil, cottonseed oil, soybean oil, coconut oil, rapeseed oil, peanut oil, olive oil, palm oil, palm kernel oil, corn oil, castor oil, sunflower seed oil, wallflower oil, and pilchard oil. The preferred oil is sesame seed oil.

The dosage of phenylephrine in the mydriatic composition of the present invention can comprise from about 0.25% by weight of the composition up to about 10% by weight of the composition which is to be topically applied to the eye. Preferably the composition is from about 0.5% by weight of the phenylephrine up to about 5% by weight of the phenylephrine. The balance of the composition is primarily the oil. However, besides the drug itself, other typically state of the art formularies such as stabilizing agents, wetting agents, antioxidants, preservatives, etc. may be added. For example, one may use from 0.25% to 0.5% of an anti-bacterial agent (chlorobutanol), from 0.01% to 0.05% of an anti-fungal agent (propylparaben, methylparaben), from 0.01% up to 0.05% of a wetting agent (poloxamer series) and from 0.01% to 0.05% of an anti-oxidant (alphatocopherol, BHA and BHT).

The following examples are offered to further illustrate but not limit the formulations of the present invention.

EXAMPLE 1

Formation of Phenylephrine Base

Phenylephrine HCl (0.3 g, 1.47 mmole) was dissolved in 3 ml of water in a test tube to which was added 1 ml of ammonia T.S. The interior of the test tube was rubbed with a glass rod to initiate the precipitation of the free base. The phenylephrine was separated by filtration and washed with about 1 ml of ice-cold water and finally dried over silica gel for 16 hours. IR (KBr) measurements were made to confirm the preparation of the phenylephrine base.

EXAMPLE 2

Preparation of an Oil Suspension of Phenylephrine and Phenylephrine HCl

| Ingredients | % (w/w composition) |
| --- | --- |
| Phenylephrine or phenylephrine HCl, U.S.P. | 1–10% |
| Pluronic P-103* | 0.05% |
| Chlorobutanol | 0.025–0.5% |
| Methylparaben | 0.05% |
| Propylparaben | 0.01% |
| Alphatocopherol** | 0.05% |
| Sesame Oil qs | 100% |

*polyethylenepolypropylene glycol or poloxamer P-103 (Wyandotte Corp., Wyandotte, Michigan)
**or other suitable oil soluble antioxidant, i.e., BHT 0.03% or BHA 0.02%

Preparation

The pluronic P-103 was added to phenylephrine or phenylephrine HCl and mixed well. Preferably, the drug powders are micronized. Each of the remaining ingredients were dissolved in about 80% of the sesame oil. If any of the ingredients are not fully dissolved, the sesame oil can be heated to about 50° for a few minutes. Upon cooling, any residual particles will be dissolved. About 10% of the sesame oil was added to the pluronic-drug mixture and triturated until the powder was wetted and well dispersed. The remainder of the sesame oil was added with stirring or trituration to form the final product which is dispensed to the patient's eye in drop form. Both phenylephrine and phenylephrine HCl form suspensions in sesame oil.

EXAMPLE 3

Mydriatic Experiments

The right eye of a normal adult New Zealand Rabbit (3–4 months) was used to measure mydriasis. A flood of diffuse light was placed at a fixed distance from the rabbit eye. The initial pupillary diameter prior to administering eye drops was about 3–4 mm. Changes in pupil diameter were measured from photographs taken with a 35 mm single lens reflex camera equipped with a close-up lens. Pupil diameters were measured at time 0 through about 5 hours. A dosing volume of 10 μl was administered to the right eye of a group of eight rabbits. A three day rest period was allowed between instillations of each formulation. Each rabbit received each formulation one time.

Figure 2:
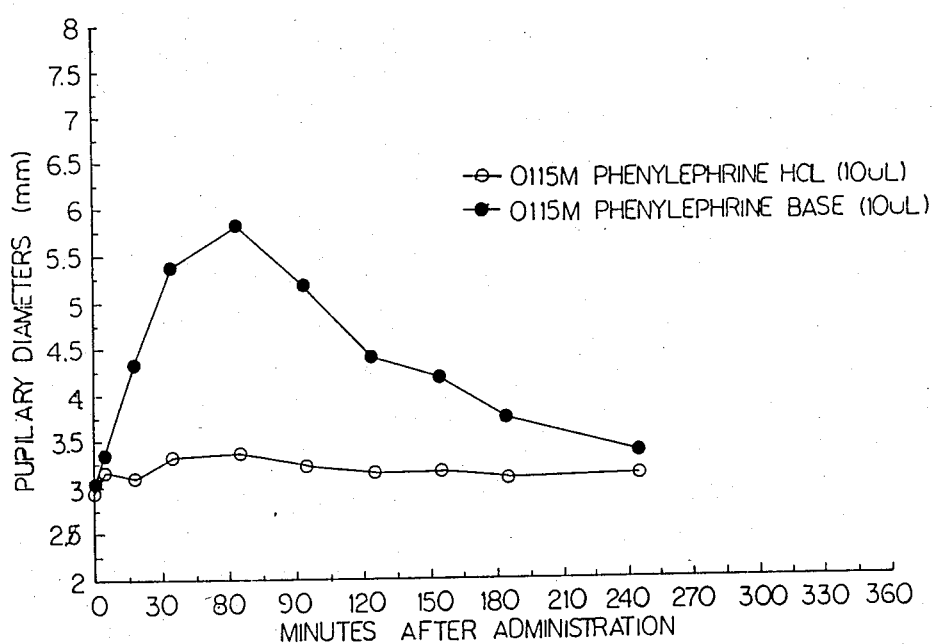
FIG. 2 shows a comparison study of phenylephrine and phenylephrine hydrochloride in sesame oil at 0.115 molar concentrations.
Figure 3:
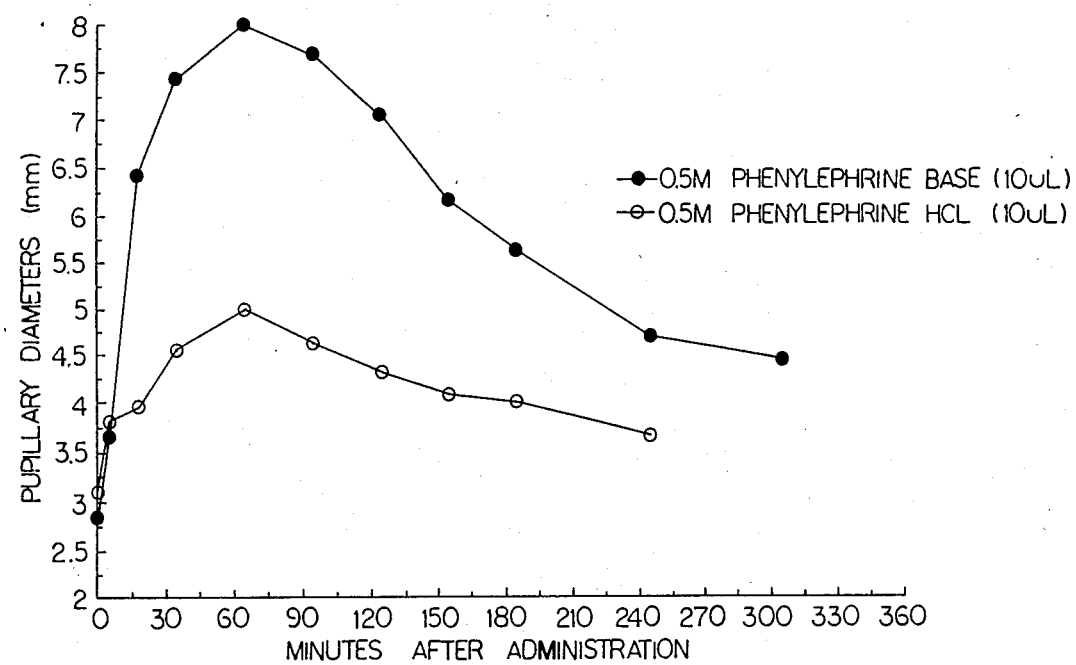
FIG. 3 shows a similar study at 0.5 molar concentrations of phenylephrine base and phenylephrine acid form in sesame oil.

FIGS. 1–3 show the results of the tests demonstrated in Examples 1–3. There it can be seen that an equimolar concentration of phenylephrine and phenylephrine hydrochloride were compared at 0.045, 0.115 and 0.5 molar. These molarities represent 1, 2.5 and 10% w/v based upon phenylephrine hydrochloride. At each concentration, the phenylephrine base yielded a greater degree of mydriasis than the hydrochloride salt at all concentrations tested.

It can therefore be seen that one can now prepare topical ocular dose form compositions of phenylephrine containing phenyleprine at less than the ordinary 10% used in the acid form composition. Moreover, it is absorbed more quickly across the eye and achieves better dilation of the pupil than same level concentrations of the acid form. As a result, compositions can be dropped down in their phenylephrine content to within the range of from 1% to 5% and still get the same mydriatic effect as those now commercially utilized. Because the concentration level is lower, the systemic side effect risk is also lower.

While not yet having been tested, it is possible that this same drug delivery system will work for other ocular drugs such as sodium sulfacetamide, pilocarpine, epinephrine, and in particular, whenever a weak base or weak acid drug is used in concentrations above 1%. Thus it can be seen that the invention accomplishes all of its stated objectives.

What is claimed is:

1. An ocular dilating composition, comprising:
   from about 0.5% by weight to about 5.0% by weight of the unionized base form of phenylephrine; and
   a non-toxic pharmaceutically acceptable oil selected from the group consisting of mineral oil and edible vegetable oil, said composition providing unionized base form of phenylephrine to the eye for preferential absorption in comparison with acid and salt forms of phenylephrine.

2. The composition of claim 1 wherein the oil is a mineral oil.

3. The composition of claim 1 wherein the base form of phenylephrine is from about 0.5% by weight to about 5% by weight of said composition.

4. The composition of claim 1 which includes from 0.25% by weight to 0.5% by weight of an anti-bacterial agent.

5. The composition of claim 1 which includes from about 0.1% by weight to 0.05% by weight of an anti-fungal agent.

6. The composition of claim 1 which includes from about 0.1% by weight to about 0.05% by weight of an anti-oxidant.

7. The composition of claim 1 which includes from about 0.1% by weight to about 0.05% by weight of a preservative.

8. The composition of claim 1 wherein the oil is a vegetable oil.

9. The composition of claim 8 wherein the oil is sesame seed oil.

10. A method of ocular drug delivery of phenylephrine which has a base form and acid/salt form, which comprises:
    placing said phenylephrine in its unionized base form;
    suspending from about 0.5% by weight to about 5.0% by weight of said phenylephrine in a non-toxic pharmaceutically acceptable oil selected from the group consisting of mineral oil and edible vegetable oil; and
    topically delivering a unit dose of said suspension which is unionized base form of phenylephrine to the eye for preferential absorption in comparison with acid and salt forms of said drug.

11. The method of claim 10 wherein said oil is a vegetable oil.

* * * * *